US007229447B1

(12) United States Patent
Biel

(10) Patent No.: US 7,229,447 B1
(45) Date of Patent: Jun. 12, 2007

(54) PHOTODYNAMIC THERAPY UTILIZING A SOLUTION OF PHOTOSENSITIZING COMPOUND AND SURFACTANT

(75) Inventor: Merrill A. Biel, Minneapolis, MN (US)

(73) Assignee: Advanced Photodynamics Technologies, Inc., Mendota Heights, MN (US)

( * ) Notice: Subject to any disclaimer, the term of this patent is extended or adjusted under 35 U.S.C. 154(b) by 0 days.

(21) Appl. No.: 09/514,070

(22) Filed: Feb. 26, 2000

Related U.S. Application Data

(63) Continuation-in-part of application No. 09/139,866, filed on Aug. 25, 1998, now Pat. No. 6,251,127.

(51) Int. Cl.
*A61B 5/02* (2006.01)

(52) U.S. Cl. .................................... 606/88

(58) Field of Classification Search ............ 606/2, 606/9, 10; 607/88, 89
See application file for complete search history.

(56) References Cited

U.S. PATENT DOCUMENTS

| 4,020,183 | A | | 4/1977 | Asculai et al. |
| 4,181,128 | A | * | 1/1980 | Swartz ..................... 607/1 |
| 4,656,186 | A | | 4/1987 | Bommer et al. |
| 4,882,234 | A | * | 11/1989 | Lai et al. .................. 514/185 |
| 4,950,665 | A | | 8/1990 | Floyd |
| 4,973,711 | A | | 11/1990 | Maienfisch |
| 5,041,078 | A | | 8/1991 | Matthews et al. |
| 5,260,020 | A | * | 11/1993 | Wilk et al. ................. 606/15 |
| 5,262,401 | A | | 11/1993 | Vogel et al. |
| 5,576,013 | A | * | 11/1996 | Williams et al. ............ 424/423 |
| 5,611,793 | A | | 3/1997 | Wilson et al. |
| 5,616,342 | A | | 4/1997 | Lyons |
| 5,676,959 | A | | 10/1997 | Heitz et al. |
| 5,827,644 | A | | 10/1998 | Floyd et al. |
| 5,882,328 | A | | 3/1999 | Levy et al. |
| 6,153,381 | A | * | 11/2000 | Rothstein .................. 435/6 |
| 6,251,127 | B1 | * | 6/2001 | Biel ........................ 607/89 |

OTHER PUBLICATIONS

"Effects of Surface-active Agents on Drug Susceptibility Levels and Ultrastructure of *Mycobacterium avium* Complex Organisms Isolated from AIDS Patients"; Sandesh P. Naik, William A. Samsonoff, and Robert E. Ruck; Diagn Microbiol Infect Dis, 1989, 11:11-19.

(Continued)

Primary Examiner—David M. Shay
(74) Attorney, Agent, or Firm—Fulbright & Jaworski L.L.P.

(57) ABSTRACT

The invention relates to a method of photoeradication of cells at a tissue site, such as an infection or sterilization site or cancer cell activity site, including applying a solution such as methylene blue, toluidene blue, polymyxin B, SDS, or other surfactants and combinations thereof to the tissue site and exposing the tissue site with a light having a light wavelength and light dosage and a light dosage rate. The solution may have a concentration of methylene blue between 5 µg/ml to about 100 µg/ml. The wavelength may range from about 610 nm to about 670 nm. The light dosage may range from about 0 J/cm$^2$ to about 200 J/cm$^2$. The light dosage rate may range from about 0 mw/cm$^2$ to about 150 mw/cm$^2$. Treatable organisms include *candida albicans, escherechia coli, pseudomonas aeruginosa, staphylococcus aureus, streptococcus pneumoniae*, and *clostridia*.

9 Claims, 1 Drawing Sheet

| Photoeradication using Methylene Blue mediated PDT & the Surfactant SDS | | | | | | | | |
|---|---|---|---|---|---|---|---|---|
| | Qualitative Colony Count | | | | | | | |
| | Score | Col. | | wave length = 664 nm | | | | |
| | 4 = | 301+. | | n/a = not applicable | | | | |
| | 3 = | 101-300. | | | | | | |
| | 2 = | 6-100. | | | | | | |
| | 1 = | 1-5. | | | | | | |
| | 0 = | 0 | | | | | | |
| | | | | | | | Single | Double |
| | Meth. Blue | | Total | Light Dose | Light Dose | No | Light | Light |
| Organism (9x10$^8$/mL) | (µg/mL) | SDS % | Power (W) | Rate (mW/cm$^2$) | (J/cm$^2$) | Light | Dose | Dose |
| Candida albicans | 100 | 0.0075 | 0.3 | 100 | 60 | 4 | 0 | 0 |
| | 100 | 0.01 | 0.3 | 100 | 60 | 4 | 1 | 0 |
| Escherchia coli | 25 | 0.003 | 0.127 | 100 | 40 | 4 | 0 | n/a |
| Pseudomonas aeruginosa | 100 | 0.003 | 0.23 | 150 | 60 | 4 | 4 | 1 |
| Staphylococcus aureus | 30 | 0.003 | 0.127 | 100 | 40 | 4 | 0 | n/a |
| | 30 | 0.005 | 0.127 | 100 | 40 | 4 | 0 | n/a |
| | 40 | 0.003 | 0.127 | 100 | 40 | 4 | 0 | n/a |
| | 40 | 0.005 | 0.127 | 100 | 40 | 4 | 0 | n/a |
| Streptococcus pneumoniae | 3 | 0.003 | 0.225 | 75 | 15 | 4 | 0 | n/a |
| | 3 | 0.005 | 0.225 | 75 | 15 | 4 | 0 | n/a |
| | 5 | 0.003 | 0.225 | 75 | 15 | 4 | 0 | n/a |
| | 5 | 0.005 | 0.225 | 75 | 15 | 4 | 0 | n/a |
| | 5 | 0.0075 | 0.225 | 75 | 15 | 4 | 0 | n/a |

OTHER PUBLICATIONS

"Differential Permeability for Lipaphilic Compounds in Uncoupler-Resistance Cells of *Escherichia coli*"; Edward G. Sedgwick and Philip D. Bragg; Biochimica et Biophysica ACTA, 1099 (1992) 45-50.

"Two Types of Haemolytic Activity of Detergents"; Jozef Bielawski; Biochimica et Biophysica ACTA, 1035 (1990) 214-217.

"Rapid Bacterial Permeabilization Reagent Useful for Enzyme Assays"; Bio Techniques; The Journal of Laboratory Technology for Bioresearch; vol. 19, No. 1 Jul. 1995.

"Review Permeabilized Cells"; Hansruedi Felix; Analytical Biochemistry 120, 211-234 (1982).

"Disruptive Effects of TRIS and Sodium Lauroyo Sarcosinate the Outer Membrane of *Pseudomonas cepacia* Shown by Fluorescent Probes"; Hosmin Anwar, Michael R.W. Brown, Adam Z. Britten, and Peter A. Lambert; The Journal of General Microbiology; vol. 129, Part 7, Jul. 1983.

"Changes in the Permeability of the Blood-Brain Barrier Following Sodium Dodecyl Sulphate Administration in the Rat"; Antonella Saija, Pietro Princi, Domenico Trombetta, Maria Lanza, Anna De Pasquale; Experimental Brain Research (1997) 115:546-551.

"Epithelial Transport of Drugs in Cell Culture. VII: Effects of Pharmaceutical Surfactant Excipients and Bile Acids on Transepitagelial Permeability in Monolayers of Human Intestinal Epithelial (CACO-2) Cells"; Eva Karin Anderberg, Christer Nystrom and Per Artursson; received Jul. 8, 1991 from the Department of Pharmaceuticals, Biomedical Centre, Uppsala University; Journal of Pharmaceutical Sciences; vol. 81, No. 9, Sep. 1992; pp. 879-887.

"Epithelial Transport of Drugs in Cell Culture. VIII: Effects of Sodium Dodecyl Sulphate on Cell Membrane and Tight Junction Permeability in Human Intestinal Epithelial (CACO-2) Cells"; Eva Karin Anderberg and Per Artursson; received Mar. 17, 1992, from the Department of Pharmaceuticals, Biomedical Center, Uppsala University; Journal of Pharmaceutical Sciences; vol. 82, No. 4, Apr. 1993; pp. 392-398.

"Do Salicylates and Ascorbate Increase the Outer Membrane Permeability to Hydrophobic Antibiotics in *Pseudomonas aeruginosa*"; Vaara M.; Drugs Under Experimental and Clinical Research; pp. 569-574, (1990).

"Agents That Increase the Permeability of the Outer Membrane"; Martti Vaara; Department of Bacteriology and Immunology, University of Helsinki, 00290 Helsinki, Finland; Microbiological Reviews, Sep. 1992, pp. 395-411.

"Fate and Effects of the Surfactant Sodium Dodecyl Sulfate"; Michael M. Singer and Ronald S. Tjeerdema; Reviews of Environmental Contamination and Toxicology, vol. 133; pp. 96-149, (1993).

"Inactivation of Gram-Negative Bacteria by Photosensitized Porphyrins"; Yeshayahu Nitzan, Mina Gutterman, Zvi Malik, and Benjamin Ehrenberg; Health Sciences Research Center, Department of Life Sciences and Department of Physics, Bar-Ilan University, Ramat-gun 52900, Israel; Photochemistry and Photobiology vol. 55, No. 1, pp. 89-96, 1992.

"pH Dependence of Sensitized Photooxidation in Micellar Anionic and Cationic Surfactants, using Thiazines Dye"; O. Bagno, H.C. Saulignac, and J.Joussot-Dubien; Photoche. Photobiol. 1979, 29(6):1079-1081.

Lasovsky, Jan, et al., "Conversions of the Light and Chemical Energies in Organized Surfactant Assemblies. Cooperative Effect of Surfactants and Photosensibilizers on Photodynamic Effect." ACTA Universitatis Palackianae Olomucensis Facultas Rerum Naturalium, 1990 vol. 97, No. Chem. 29, pp. 37-44. XP001053724 Tables, Figures 3, 4, p. 41, p. 42, abstract.

Bacirova, Martina, et al., "Protection Effect of Physiological Antioxidants and Surface Active Substances Against the Harmful Effects of Radiation on Paramecium Caudatum." ACTA Universitatis Palackianae Olomucensis Facultas Rerum Naturalium, 1993 vol. 112 89-95, XP001052803, p. 89, Paragraph Introduction, Tables 1,3, Abstract.

Norris M.J., et al., "Cell Envelope Composition and Sensitivity of *Proteus mirabilis, Pseudomonas aeruginosa* and *Serratia marcescens* to Polymyxin and Other Antibacterial Agents." Letters in Applied Microbiology, 1985, vol. 1, No. 1, pp. 3-6, XP001042384, Table 1.

Kropinski A.M.B., et al., "Susceptibility of Lipopolysaccharide-Defective Mutants of *Pseudomonas aeruginosa* Strain PAO to Dyes, Detergents, and Antibiotics." Antimicorbial Agents and Chemotherapy, 1978, vol. 13, No. 3, pp. 494-499, XP001042385, p. 469, Left-hand Column.

Kapoor, R.C., "Dye-Surfactant Interactions. A Spectral Study." J. Indian Chem. Soc., 1986, vol. 63, No. 6, pp. 541-546, XP001053295, pp. 542-545, p. 545, Paragraph Discussion.

Zhang, Hong-Man, et al., "Study on the Dimer-Monomer Equilibrium of a Florescent Dye and its Application in Nucleic Acids Determination." Anal. Chim. ACTA, 1998, vol. 361, No. 1-2, pp. 9-17, XP001053292, Figures 2, 3.

Wakayama, Y., et al., "Gene Responsible for Protecting *Escherichia-coli* From Sodium Dodecyl Sulfate and Toluidine Blue Plus Light." Journal of Bacteriology, vol. 159, No. 2, 1984, pp. 527-532, XP001052816, ISSN: 0021-9193, p. 531, Paragraph Discussion.

Takagi M., et al., A Gene Responsible for Protecting *Escherichia-coli* From Sodium Dodecyl Sulfate and Toluidine Blue Plus Light. Journal of Radiation Research, vol. 26, No. 1, 1985, p. 32, Abstract a-C-2 XP001052834, ISSN: 0449-3060.

Murgia S.M., et al., Laser Photolysis of Methylene blue in Aquesous Micellar Systems. Photobiochemistry and Photobiophysics, vol. 5, No. 1, 1983, pp. 53-60, XP001052806, ISSN: 0165-8646, Abstract, Figures, Tables, pp. 59-60.

Dahmiwal N. R., et al., "Dye-Sensitized Photooxygenation of Diphenylamine in SDS Micellar Solution." Indian Journal of Chemistry Section an Inorganic Bio-Inorganic Physical, vol. 30, No. 8, 1991, pp. 660-664, XP001052817, 1991, ISSN: 0019-5103, Abstract Figures.

Gorman A. A., et al., "The Photo Sensitized Formation and Reaction of Singlet Molecular Oxygen in Aqueous Micellar Systems." Photochemistry and Photobiology, vol. 23, No. 6, 1976, pp. 399-403, XP001052818, ISSN: 0031-8655, Abstract, Figures.

Bagno, O., et al., "PH Dependence of Sensitized Photooxidation in Micellar Anionic and Cationic Surfactants, using Thiazines Dyes." Photochem. Photobiol., 1979, vol. 29, No. 6, pp. 1079-1081, XP001052841, Abstract, p. 1079, Left-hand Column.

Lasovsky, Jan, et al., "The Enhancement of Flourescence in Micellar Solutions of Ion Surfactants." ACTA Univ. Palacki. Olomuc., FAC. Rerum Nat., 1986, vol. 85, No. Chemica, 25, pp. 47-54, XP001053320, Figures 1, 2, Table 1, p. 49, Last Paragraph—p. 52, Last Line.

Kalab D., "Photodynamic Inactivation of Some *Bacillus subtilis* Bacteriophages." Experientia, Mar. 15, 1967, vol. 23, No. 3, pp. 181-182, XP001042399.

Mainwright M., et al., "Photobactericidal Activity of Phenothiazinium Dyes Against Methicillin-Resistant Strains of *Staphylococcus aureus*." FEMS Microbiology Letters, Mar. 15, 1998, vol. 160, No. 2, pp. 177-181, XP001042387 Abstract, Tables.

Mainwright M., et al., "A Study of Photobactericidal Activity in the Phenothiazinium Series." FEMS Immunology and Medical Microbiology, Sep. 1997, vol. 19, No. 1, pp. 75-80, XP001042388, Abstract, pp. 77-79, Paragraph Results and Discussion.

Konig, K., et al., "Photodynamische Aktivitat Von Methylenblau." Aktuelle Dermatologie, 1993, vol. 19, No. 7, pp. 195-198, XP001052840, p. 196, Right-hand Column, Last Paragraph, Figure 3.

Lorenz, M., et al., "High Doses of Methylene Blue/Light Treatment Crosslink the A-Alpha-Subunit of Fibrinogen: Influence of this Photooxidation on Fibrinogen Binding to Platelets." Haemostasis, vol. 28, No. 1, Jan. 1998, pp. 17-24, XP001042343, ISSN: 0301-0147, Abstract, p. 18, Paragraph Introduction, p. 22, Paragraph Discussion, p. 24.

Wagner, S. J., et al., "Preservation of Red Cell Properties after Virucidal Phototreatment with Dimethylmethylene Blue." Transfusion, vol. 38, No. 8, Aug. 1998, pp. 729-737, XP001052839, ISSN: 0041-1132, Abstract, Tables, Figures.

Amstey, Ms., "Current Concepts of Herpesvirus Infection in the Woman." AM. Journal Obstet. Gynecol., vol. 117, No. 5, 1973, pp. 717-725, XP001042386, p. 724, Left-hand Column, Last Paragraph—Right-hand Column, Line 5.

Caldas, L.R., et al., "Antiviral Action by Photodynamic Effect on Bacterial Systems: Special Sensitivity of Infected Bacteria!" Comptes Rendus Hebdomadaires Des Seances De L'Academie Des Sciences. Serie D: Sciences Naturelles, Apr. 29, 1974, vol. 278, No. 18, pp. 2369-2372, XP001052858, France, Abstract, Figures 1, 2, p. 2372, Paragraph Remarque.

Savino, A., et al. "Photodynamic Inactivation of *E. coli* and *B. subtilis* by Free and Immobilized Methylene Blue" Bollettino Della Societa Italiana Di Biologia Sperimentale, 1981, vol. 57, No. 15, pp. 1601-1707, XP001052805, Italy, Tables 1, 2.

Sugioka, H., et al., "Micelle Formation of Sodium Cholate and Solubilization into the Micelle" Biochemica et Biophysica Acta 1394 (1998), pp. 99-110.

Albalak, A., et al., "Effects of Submicellar Bile Salt Concentrations on Biological Membrane Permeability to Low Molecular Weight Non-Ionic Solutes." Biochemistry, vol. 35, No. 24, 1996, pp. 7936-7945.

Danner, et al., "Purification, Toxicity, and Antiendotoxin Activity of Polymyxin B Nonapeptide" Antimicrobial Agents and Chemotherapy, Sep. 1989, pp. 1428-1434.

E.L. Gyenge and C.W. Oloman, Influence of surfactants on the electroreduction of oxygen to hydrogen peroxide in acid and alkaline,electrolytes, Journal of Applied Electrochemistry 31: 233-243, 2001.

Reddi, et al., "Flash Photolysis Studies of Hemato- and Copro-Porphyrins in Homogeneous and Microheterogeneous Aqueous Dispersions," Photochemistry and Photobiology, vol. 38, No. 6., pp. 639-645, 1983.

* cited by examiner

Photoeradication using Methylene Blue mediated PDT & the Surfactant SDS

| | Qualitative Colony Count | | | | | | | | |
|---|---|---|---|---|---|---|---|---|---|
| | Score | Col. | | wave length = 664 nm | | | | | |
| | 4 = | 301+. | | n/a = not applicable | | | | | |
| | 3 = | 101-300. | | | | | | | |
| | 2 = | 6-100. | | | | | | | |
| | 1 = | 1-5. | | | | | | | |
| | 0 = | 0 | | | | | | | |
| | Meth. Blue | | Total | Light Dose | Light Dose | | Single | Double |
| Organism (9x10⁸/mL) | (µg/mL) | SDS % | Power (W) | Rate (mW/cm²) | (J/cm²) | No Light | Light Dose | Light Dose |
| Candida albicans | 100 | 0.0075 | 0.3 | 100 | 60 | 4 | 0 | 0 |
| | 100 | 0.01 | 0.3 | 100 | 60 | 4 | 1 | 0 |
| Escherichia coli | 25 | 0.003 | 0.127 | 100 | 40 | 4 | 0 | n/a |
| Pseudomonas aeruginosa | 100 | 0.003 | 0.23 | 150 | 60 | 4 | 4 | 1 |
| | 30 | 0.003 | 0.127 | 100 | 40 | 4 | 0 | n/a |
| Staphylococcus aureus | 30 | 0.005 | 0.127 | 100 | 40 | 4 | 0 | n/a |
| | 40 | 0.003 | 0.127 | 100 | 40 | 4 | 0 | n/a |
| | 40 | 0.005 | 0.127 | 100 | 40 | 4 | 0 | n/a |
| Streptococcus pneumoniae | 3 | 0.003 | 0.225 | 75 | 15 | 4 | 0 | n/a |
| | 3 | 0.005 | 0.225 | 75 | 15 | 4 | 0 | n/a |
| | 5 | 0.003 | 0.225 | 75 | 15 | 4 | 0 | n/a |
| | 5 | 0.005 | 0.225 | 75 | 15 | 4 | 0 | n/a |
| | 5 | 0.0075 | 0.225 | 75 | 15 | 4 | 0 | n/a |

*FIG. 1*

PHOTODYNAMIC THERAPY UTILIZING A SOLUTION OF PHOTOSENSITIZING COMPOUND AND SURFACTANT

RELATED APPLICATION

This application is a continuation-in-part application based on application Ser. No. 09/139,866 filed Aug. 25, 1998, now U.S. Pat. No. 6,251,127, the benefit of the priority date is hereby claimed pursuant to 35 U.S.C. §120.

FIELD OF THE INVENTION

The invention relates to a photodynamic therapy (PDT), and more particularly to a photodynamic therapy utilizing a combined solution of a photosensitizing compound and surfactant compound. Still more specifically, the invention relates to photodynamic inactivation of bacteria, fungal, and viral wound infections and sterilization of tissue using methylene blue or toluidene blue and a surfactant, such as polymyxin-B or SDS. Additionally, the invention relates to photodynamic eradication of cancer cells, such as present within a tumor, by PDT in conjunction with an administration of a solution including a photodynamic sensitizing compound and a surfactant. The present invention advantageously uses light energy in combination with a photosensitizing agent and a surfactant solution to treat both invitro and invivo pathologens, including cancer cells and microbiological pathogens.

BACKGROUND OF THE INVENTION

Abnormal cells in the body are known to selectively absorb certain dyes delivered to a treatment site to a more pronounced extent than surrounding tissue. Once presensitized, the cancerous or abnormal cells can be destroyed by irradiation with light of an appropriate wavelength corresponding to an absorbing wavelength of the dye, with minimal damage to surrounding normal tissue. This procedure, which is known as photodynamic therapy (PDT), has been clinically used to treat metastatic breast cancer, bladder cancer, head and neck cancers, and other types of malignant tumors.

SUMMARY OF THE INVENTION

The present invention provides a method of photoeradication of cells at a tissue site, such as during an invitro or invivo disinfection procedure, or during a sterilization procedure, or for cancer cell destruction. The method utilizes a combined solution of a photosensitizing dye and a surfactant compound. The invention provides a method of disposing the combined solution at or near the tissue site and subsequently irradiating the tissues site with laser light at a wavelength absorbed by the photosensitizing dye.

The invention relates to use of a photosensitizing agent, such as methylene blue or toluidene blue, in combination with a surfactant compound, such as polymyxin B or SDS, in a PDT treatment protocol against bacterial or fungal infections or for cancer cell photoeradication. A treatment device is configured to deliver light energy to the area of infection at wavelengths ranging from about 450 nm to about 850 nm; provide a dosage rate ranging from about 0 to about 150 mw/cm$^2$; and provide a light dose ranging from 0 to about 300 J/cm$^2$.

The use of a photosensitizer, e.g., methylene blue or toluidene blue, combined with a surfactant compound, such as SDS or polymyxin B, in a photodynamic therapy advantageously acts as a broad spectrum antimicrobial, i.e., antibacterial, antiviral, and antifungal agent. The dye/surfactant combination and PDT may be used, for example, before a surgical operation. The present invention advantageously results in the destruction of gram positive and gram negative bacteria and fungus. Importantly, the present invention acts to destroy antibiotic resistant bacteria as it utilizes a different destruction mechanism than antibiotics.

The invention relates to a method of treating an infection including identifying an in-vivo area of infection; applying a concentration including a photosensitizing dye, such as methylene blue or toluidene blue, and a surfactant, such as polymyxin B or SDS, to the area of infection; and exposing the area of infection with a light having a light wavelength, light dosage and a light dosage rate. The light wavelength may range from about 610 nm to about 680 nm. The light dosage may range from about 10 J/cm$^2$ to about 60 J/cm$^2$. The light dosage rate may range from about 50 mw/cm$^2$ to about 150 mw/cm$^2$. The wavelength may range from about 630 nm to about 664 nm. The concentration may range from about 10 µg/ml to about 500 µg/ml. The area of infection may include gram positive and gram negative bacteria, fungus, or virus including, but not limited to, at least one of *staphylococcus, candida albicans, escherichia coli, enterococcus, streptococcus, pseudomonus aeruginosa, hemophilus* influenzae, or *clostridia*.

The invention also relates to a treatment kit including a volume of a concentration including at least a combination of methylene blue or toluidene blue and polymyxin B or SDS. The concentration ranges from about 3 µg/ml to about 500 µg/ml. Also included is a light emitting treatment device. The light emitting treatment device is configured to emit at wavelengths ranging from about 450 nm to about 850 nm; provide a dosage rate ranging from about 0 to about 150 mw/cm$^2$; and provide a light dose ranging from 0 to about 300 J/cm$^2$.

The invention also relates to a method of treating an infection, an invitro or invivo sterilization procedure, or photoeradication of cancer cells, including providing one or more cells; disposing a concentration of combined dye/surfactant on the one or more cells; applying a light having a wavelength ranging from about 450 nm to about 850 nm; a dosage rate ranging from about 0 to about 150 mw/cm$^2$; and a light dose ranging from 0 to about 300 J/cm$^2$ to the one or more cells wherein the combination of light and dye is adapted to cause photodestruction of the one or more cells. The one or more cells may be a bacteria, virus, a fungus, or cancer cells. The one or more cells may be gram positive or gram negative. The dye may be methylene blue, toluidene blue, or a combination thereof. The dye may be monomeric or dimeric.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTIONS OF THE DRAWINGS

FIG. 1 is a table of results of photodynamic photoeradication using a combined solution of methylene blue and the surfactant, SDS.

DETAILED DESCRIPTION OF THE INVENTION

In accordance with the invention, a photodynamic therapy is provided utilizing a photosensitizing agent such as methylene blue or toluidene blue in combination with a surface acting agent or 'surfactant' and a light emitting treatment device such as a light wand, light patch, light pad or shaped light-emitting article such as a mouthpiece to illuminate the site.

The present invention may be used in conjunction with or in relation to inventions disclosed in the following applications of the applicant, including:

Method of Enhancing Photodynamic Therapy by Administering an Immunologic Adjuvant, U.S. patent application Ser. No. 09/139,861, pending;

Expandable Treatment Device for Photodynamic Therapy and Method of Using Same, U.S. patent application Ser. No. 09/239,353, pending;

Spatial Orientation and Light Sources and Method of Using Same for Medical Diagnosis and Photodynamic Therapy, U.S. patent application Ser. No. 09/139,862, now U.S. Pat. No. 6,048,359; and Treatment Device for Topical Photodynamic Therapy and Method of Making Same, PCT/US9817589, WO 99/10046, pending.

All documents within these applications are herein incorporated by reference in their entireties for all purposes.

Photosensitizing dyes and compounds for use in accordance with the present invention are generally non-toxic to the target microbes and surrounding tissues at concentrations envisaged. However, there is no particular requirement that the photosensitizers should be non-toxic to the microbes. Particular photosensitizers which may be used in accordance with the invention include dyes and compounds such as methylene blue and toluidene blue.

Surface acting agents, or surfactants, are defined as substances which alter the energy relationship at interfaces. Among the manifestations of these altered energy relationships is the lowering of surface or interfacial tensions. Compounds displaying surface activity are characterized by an appropriate structural balance between one or more water-attracting groups and one or more water-repellent groups. Surfactants characterized by having two different moieties, one polar and the other nonpolar. The polar moeity is referred to as hydrophilic or lipophobic, and the nonpolar as hydrophobic or lipophilic. The electrical charge on the hydrophilic portion of a surface acting agent may serve as a convenient basis of classification of these compounds. Surface active agents have been classified as: Anionic, Cationic, Non-Ionic, and Amphoteric. Surfactants are known to affect the permeability of cell membranes. The ability of surfactants to become oriented between lipid and protein films is thought to produce a disorientation of the lipoprotein membrane of microorganisms, so that it no longer functions as an effective osmotic barrier. The polymixins, colisimethate, and the polyene antifungal agents nystatin and amphotericin are surfactants, as is sodium dodecyl sulfate (SDS).

A photosensitizing dye compounds such as methylene blue or toluidene blue may be used in combination with surfactants, such as SDS and polymyxin B, and activated by light energy at approximately 630-660 nm wavelengths to provide broad spectrum antibiotic activity for destroying both gram positive and gram-negative bacteria, fungus, virus and cancer cells. The dye compound and surfactant may be combined in solution and administered to a site to be treated. Solution administration may include topical application, or intravenous, subcutaneous, intratumor, or peritumoral injection. Additional administration approaches may also be practicable. An intratumoral injection of the solution may be advantageous for photoeradication of tumor cells.

A particular treatment protocol utilizing the photosensitizer methylene blue and SDS concentrations from 0.001% to 0.01% has been identified as advantageous in the destruction of certain microorganisms, such as candida albicans, escherechia coli, pseudomonas aeruginosa, staphylococcus aureus, and streptococcus pneumoniae.

Reference may be made to FIG. 1, which illustrates a schedule of results for an investigation according to the present invention of photoeradication using methylene blue mediated PDT and the surfactant, SDS, at a wavelength of approximately 664 mm. The laser used was a diode laser with a power output of 1000 mW. Methylene blue concentrations range from 5 to 100 µg/ml. SDS concentrations range from 0.003 to 0.01%. Light power ranges from 0.127 to 0.3 watts. The combined solution was topically applied at the cell site. Light dosage rates range from 75 to 100 mW/cm2. Light dosages range from 15 to 60 J/cm2. A qualitative colony count relates particular colony counts to an associated score. For instance, a qualitative colony count of 5 would yield a score of '1', while a colony count of 151 would have an associated score of '3'. The results of this investigation demonstrated that the solution including a surfactant and a photosensitising agent can sensitize several species of bacteria to killing by diode laser irradiation.

A laser light source may be used to practice the present invention. A variety of light sources are currently available, and the selection of a particular laser light source for implementing the PDT would readily be appreciated by those skilled in the relevant arts. The laser source will be selected having regard to the choice of wavelength, beam diameter, exposure time and sensitivity of the microbes to the laser/photosensitizer/surfactant combination.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A method of photodynamic disruption of cells comprising the steps of:
    identifying an area of cell activity;
    applying a concentration including a combination of a surfactant and a photosensitizing agent to the area of cell activity, said surfactant disorienting a cell membrane so that said membrane no longer functions as an effective osmotic barrier, and so that said photosensitizing agent is able to pass through the disoriented cell membrane; and
    exposing the area of cell activity to light having a light wavelength, light dosage and a light dosage rate to cause photodynamic cellular disruption, wherein the surfactant is SDS provided in a solution having an SDS concentration range of between 0.003% to 0.01%.

2. The method of photodynamic disruption of cells of claim 1 wherein the step of identifying an area of cell activity includes an examination of a portion of a living body.

3. The method of photodynamic disruption of cells of claim 1 wherein the light wavelength ranges from about 400 nm to about 800 nm, the light dosage ranges from about 10 $J/cm^2$ to about 100 $J/cm^2$ and the light dosage rate ranges from about 50 $mw/cm^2$ to about 200 $mw/cm^2$.

4. The method of photodynamic disruption of cells of claim 1 wherein the wavelength ranges from about 600 nm to about 700 nm.

5. A method of photodynamic disruption of acellular organisms comprising the steps of:
   identifying an area of acellular organism activity;
   applying a concentration including a combination of a surfactant and a photosensitizing agent to the area of acellular organism activity, said surfactant disorienting an acellular organism membrane so that said membrane no longer functions as an effective osmotic barrier, and so that said photosensitizing agent is able to pass through the disoriented acellular organism membrane; and
   exposing the area of acellular organism activity to light having a light wavelength, light dosage and a light dosage rate, wherein the surfactant is SDS provided in a solution having an SDS concentration range of between 0.003% to 0.01%.

6. The method of photodynamic disruption of acellular organisms of claim 5 wherein the step of identifying an area of acellular activity includes the step of identifying an area of virus activity.

7. The method of photodynamic disruption of acellular organisms of claim 5, wherein the step of identifying an area of acellular organism activity includes an examination of a portion of a living body.

8. The method of photodynamic disruption of acellular organisms of claim 5, wherein the light wavelength ranges from about 400 nm to about 800 nm, the light dosage ranges from about 10 $J/cm^2$ to about 100 $J/cm^2$ and the light dosage rate ranges from about 50 $mw/cm^2$ to about 200 $mw/cm^2$.

9. The method of photodynamic disruption of acellular organisms of claim 5 wherein the wavelength ranges from about 600 nm to about 700 nm.

\* \* \* \* \*